United States Patent [19]

Hoke et al.

[11] Patent Number: 4,849,328

[45] Date of Patent: * Jul. 18, 1989

[54] CYAN DYE-FORMING COUPLERS AND PHOTOGRAPHIC MATERIALS CONTAINING SAME

[75] Inventors: David Hoke; Kenneth N. Kilminster, both of Rochester, N.Y.

[73] Assignee: Eastman Kodak Company, Rochester, N.Y.

[*] Notice: The portion of the term of this patent subsequent to Oct. 4, 2005 has been disclaimed.

[21] Appl. No.: 160,461

[22] Filed: Feb. 25, 1988

[51] Int. Cl.$^4$ ................................................ G03C 7/34
[52] U.S. Cl. ...................................... 430/553; 430/552
[58] Field of Search ................................ 430/552, 553

[56] References Cited

U.S. PATENT DOCUMENTS

| | | | |
|---|---|---|---|
| 4,333,999 | 6/1982 | Law | 430/17 |
| 4,579,813 | 4/1986 | Aoki et al. | 430/553 |
| 4,609,619 | 9/1986 | Katoh et al. | 430/553 |

FOREIGN PATENT DOCUMENTS

| | | | |
|---|---|---|---|
| 111643 | 7/1984 | Japan | 430/553 |
| 111644 | 8/1984 | Japan | 430/553 |
| 105644 | 10/1984 | Japan | . |
| 168155 | 7/1987 | Japan | 430/553 |
| 195656 | 8/1987 | Japan | 430/553 |

*Primary Examiner*—Paul R. Michl
*Assistant Examiner*—Lee C. Wright
*Attorney, Agent, or Firm*—Thomas F. Kirchoff

[57] ABSTRACT

Novel phenolic cyan dye-forming couplers are disclosed. The coupler compounds contain a p-cyanophenylureido group in the 2- position and an acylamino group in the 5- position of the phenolic ring. The acylamino group contains bulky substituents to provide steric interaction within the coupler molecule as well as within the dye molecule derived therefrom. The coupler compounds are useful in photographic recording materials.

11 Claims, No Drawings

CYAN DYE-FORMING COUPLERS AND PHOTOGRAPHIC MATERIALS CONTAINING SAME

The present invention relates to a photographic material containing a phenolic cyan dye-forming coupler. More particularly, this invention relates to couplers which are used to obtain cyan dyes for color photography which couplers are typically phenols and napthtols and which couplers yield azomethine dyes upon coupling with oxidized aromatic primary amino color developing agents.

U.S. Pat. No. 4,333,999 describes cyan phenolic couplers which comprise a p-cyanophenylureido group in the 2-position of the phenolic ring. These couplers have highly desirable properties in that they can provide dyes of excellent purity and hues which are shifted bathochromically to the long wavelength red absorption region. However, even with these couplers, which have found extensive utility, further improvements in coupler reactivity and enhanced dye absorption continue to be sought. For example, it has been difficult to obtain, with the same coupler, both high coupling effectiveness and a dye having the desired hue purity plus long wavelength red absorption. Coupling effectiveness is measured by comparing the gamma or contrast of its dye image sensitometric test curve with that of a control coupler under identical conditions.

The presence of sulfone ($-SO_2-$) groups in ballast moieties of cyan coupler compounds has been described in various publications. These publications include Japanese Patent Publication Nos. 105644/1984 (priority of Dec. 10, 1982), 111643/1984 and 111644/1984 (both having priorities of Dec. 17, 1982). Couplers having sulfone groups in the ballast moiety are also disclosed in U.S. Pat. No. 4,609,619 and are described therein as being effective in reducing cyan dye loss when photographic materials containing cyan images are subjected to fatigued bleach or bleach-fix solutions.

The coupler structures described in these publications do not disclose or suggest the combination of moieties which provide improved coupling effectiveness while maintaining deep wavelength absorption in the red region of the visible spectrum and hue purity in subsequently obtained cyan dyes.

Accordingly, couplers are continually being sought which can provide cyan dyes having narrow half-bandwidths (HBW) for improved hue purity, which have long wavelength absorption in the red region of the visible spectrum thereby avoiding unwanted green absorption and which possess desirable coupling effectiveness values.

These objectives are provided in accordance with the present invention which resides in the use of particular substituent combinations in the 5-position acylamino ballast moiety of cyan phenolic coupler compounds of the general type described in U.S. Pat. No. 4,333,999. The coupler compounds of this invention alter the sulfone ($SO_2$) group of the prior art compounds and are employed with a particular combination of substituent groups adjacent to the modified sulfone group. The combination includes use of at least one bulky group substituent which is believed to be capable of providing steric interaction with other portions of the coupler compound as well as in the resulting image dye. The results achieved reflect improved hue purity while retaining at least comparable coupling effectiveness plus desired long wavelength absorption in the red region of the visible spectrum.

Coupler compounds which fulfill the requirements noted above, and which fall within this invention, have the following structural formula:

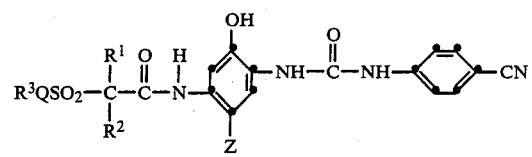

wherein:
Q is oxo or $-NR^4-$;
$R^1$ is an unsubstituted or a substituted, straight or branched chain alkyl group having from 1 to about 20 carbon atoms, an unsubstituted or a substituted cycloalkyl group having from 3 to about 8 carbon atoms in the ring, an alkylcarbonyl or an alkoxycarbonyl group having from 1 to about 20 carbon atoms in the alkyl or the alkoxy moiety;
$R^2$ is as defined for $R^1$ or is hydrogen;
$R^3$ is an unsubstituted or a substituted alkyl group having from 1 to about 24 carbon atoms, an unsubstituted or a substituted cycloalkyl group having from 3 to about 8 carbon atoms in the ring, an unsubstituted or a substituted aryl group having from 6 to about 24 carbon atoms, or an unsubstituted or a substituted heterocyclic group having from 3 to about 8 atoms in the heterocyclic ring, wherein the hetero ring atoms can be nitrogen, oxygen, or sulfur;
with the proviso that when $R^3$ is a primary alkyl group, $R^1$ must contain at least 2 carbon atoms;
$R^4$ is hydrogen, an unsubstituted or a substituted alkyl group having from 1 to about 24 carbon atoms, an unsubstituted or a substituted cycloalkyl group having from 3 to about 8 carbon atoms in the ring, or an unsubstituted or a substituted aryl group having from 6 to about 24 carbon atoms; and
Z is hydrogen or a coupling off group.

At least one of $R^1$, $R^2$, $R^3$ and $R^4$ is of such size and configuration as to confer sufficient bulk to the coupler molecule to provide desired steric interaction believed responsible for the effects seen in the coupler compounds described herein. In combination, these R group substituents must also provide sufficient ballast to render the coupler compound substantially nondiffusible in the layer of a photographic imaging material in which it is coated.

The specific combination in a phenolic coupler of (a) a para-cyanophenylureido group in the 2-position and (b) a modified sulfone-containing ballast group in the 5-position, as described above, provides dyes having improved hue purity while retaining high coupling effectiveness and long wavelength red light absorption. These results are surprising and could not have been predicted from the body of knowledge available before the investigations leading to this invention were carried out.

In preferred coupler compounds of this invention $R^1$ is alkyl of 1 to about 20 carbon atoms and $R^2$ is alkyl of 1 to about 4 carbon atoms. In particularly preferred coupler compounds $R^1$ is alkyl of 1 to about 14 carbon atoms and $R^2$ is hydrogen. When the $R^1$ and $R^2$ groups are substituted, such substituents include hydroxy, halogen, or alkoxy having from 1 to about 8 carbon atoms.

When the $R^3$ or $R^4$ groups are substituted such substituents may include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido and sulfamoyl groups wherein the alkyl and aryl substituents, and the alkyl and aryl moieties of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido and sulfamoyl substituents can contain, respectively, from 1 to about 30 carbon atoms and from 6 to about 30 carbon atoms and can be further substituted with such substituents.

Coupling off groups defined by Z are well known to those skilled in the art. Such groups can determine the equivalency of the coupler i.e., whether it is a 2-equivalent coupler or a 4-equivalent coupler. Such groups can also modify the reactivity of the coupler or can advantageously affect the layer in which the coupler is coated, or other layers in a photographic recording material, by performing, after release from the coupler, such functions as development inhibition, bleach inhibition, bleach acceleration, color correction and the like.

Representative classes of coupling-off groups include alkoxy, aryloxy, heteroyloxy, sulfonyloxy, acyloxy, acyl, heterocyclyl, sulfonamido, phosphonyloxy and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U. K. patents and published application Nos. 1,466,728, 1,531,927, 1,533,039, 2,006,755A and 2,017,704A, the disclosures of which are incorporated herein by reference.

Examples of preferred coupling-off groups which can be represented by Z are:

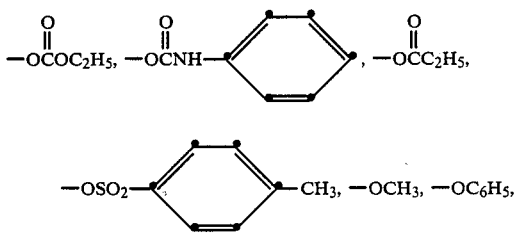

-continued

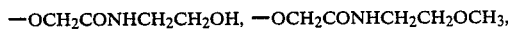

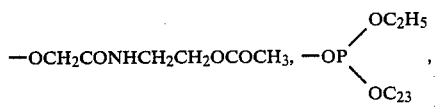

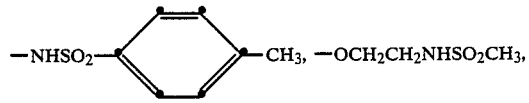

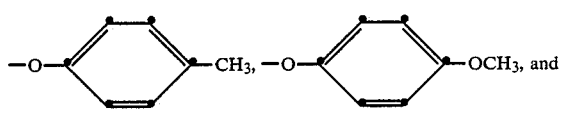

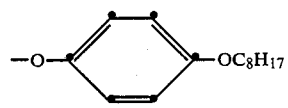

Especially preferred Z groups are hydrogen and

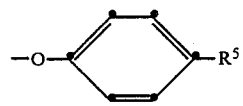

where $R^5$ is an alkyl or an alkoxy group having from 1 to about 10 carbon atoms.

The desirable objectives of this invention are attained by particular combinations of substituent groups on the ballast moiety of the coupler compounds. For example, bulky substituent groups, when present in at least one of the positions represented by $R^1$, $R^2$, $R^3$ and $R^4$, which substituents are spatially arranged so that steric interaction between them and the $SO_2$ moiety, or with adjacent position substituents on the coupler molecule, result in cyan dyes having desirably narrow bandwidths while absorbing red light at relatively longer wavelengths.

Specific coupler compounds of this invention are shown below in Table 1 with reference to the following structural formula:

TABLE 1

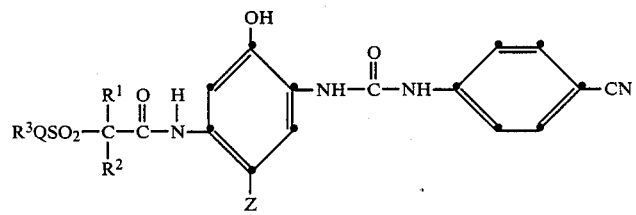

| Coupler Compound | $R^1$ | $R^2$ | $R^3$ | Q | Z* |
|---|---|---|---|---|---|
| 1 | $-C_2H_5$ | H | $-C_{16}H_{33}$ | $-O-$ | A |
| 2 | $-C_3H_7-i$ | " | $-C_{16}H_{33}$ | $-O-$ | " |
| 3 | $-C_{14}H_{29}$ | " | $-CH_3$ | $-O-$ | " |
| 4 | $-C_4H_9$ | " | $-C_{18}H_{37}$ | $-O-$ | " |
| 5 | $-C_{10}H_{21}$ | " | $-C_{18}H_{37}$ | $-O-$ | " |
| 6 | $-C_3H_7$ | " | $-C_{12}H_{25}$ | $-O-$ | A |
| 7 | $-C_2H_4Cl$ | " | $-C_{16}H_{33}$ | $-O-$ | B |
| 8 | $-C_2H_5$ | H | $-C_{12}H_{25}$ | $-NH-$ | A |

TABLE 1-continued

[Structure: R³QSO₂—C(R¹)(R²)—C(=O)—NH— (phenyl with OH at 2-position, Z at 5-position, NH-C(=O)-NH at 3-position linked to phenyl-CN)]

| Coupler Compound | R¹ | R² | R³ | Q | Z* |
|---|---|---|---|---|---|
| 9 | —CH₃ | —CH₃ | phenyl-NHSO₂C₁₆H₃₃ | —NH— | B |
| 10 | —C₂H₅ | H | " | —NH— | A |
| 11 | —C₂H₅ | " | phenyl with NHSO₂C₁₆H₃₃ | —NH— | " |
| 12 | —C₁₀H₂₁ | " | phenyl-NHSO₂-phenyl-COOH | —NH— | " |
| 13 | —C₁₀H₂₁ | " | phenyl-NHSO₂-phenyl-OH | —NH— | " |
| 14 | —C₂H₅ | " | phenyl-C₁₅H₃₁ | —O— | A |
| 15 | —C₂H₅ | " | —C₁₈H₃₇ | —NCH₃— | H |

*A = —O-phenyl-OCH₃

B = —O-phenyl-OC₈H₁₇

Couplers of this invention can be prepared by reacting p-cyanophenylisocyanate with an appropriate aminophenol, such as 2-amino-5-nitrophenol or 2-amino-4-chloro-5-nitrophenol to form the 2-(p-cyanophenyl)ureido compound. The nitro group can then be reduced to an amine, and the ballast group attached thereto by conventional procedures. Two equivalent couplers can be prepared by known techniques, for example, by substitution of the 4-chloro group on the starting phenol or by a synthetic route shown below in the preparation of Coupler Compound No. 1 of this invention.

SYNTHESIS 1

Preparation of Coupler Compound No. 1 was accomplished according to the following synthetic scheme:

A. Preparation of phenolic coupler moiety (S-4)

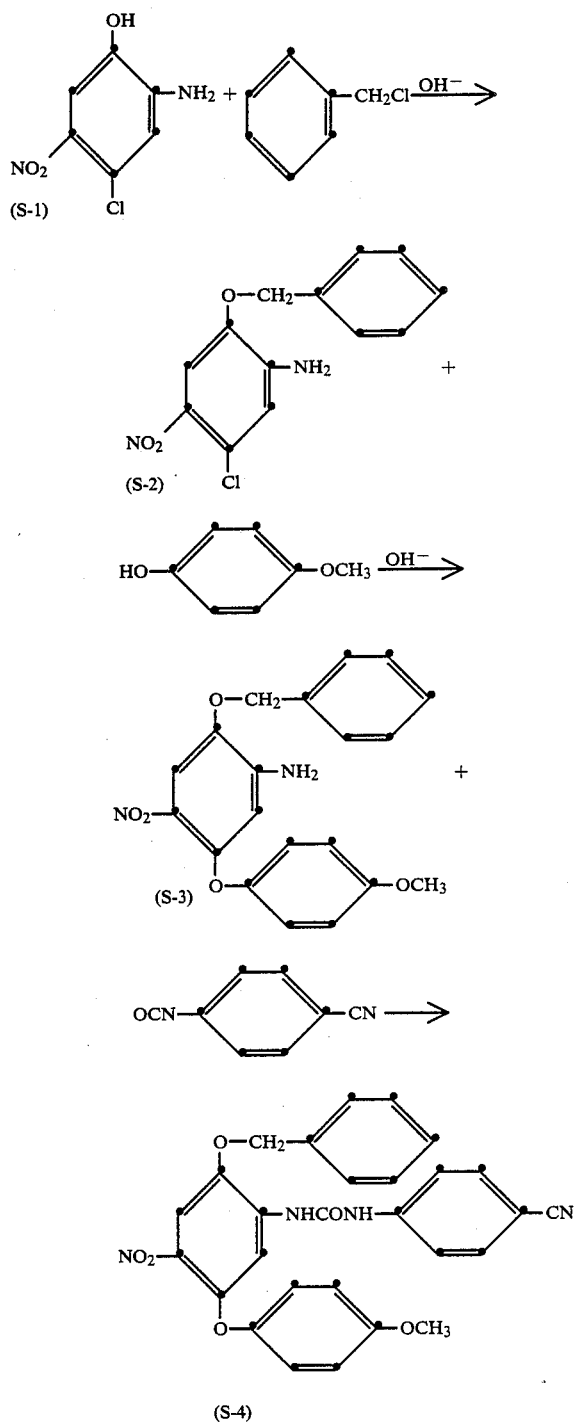

Preparation of the blocked 2-p-cyanophenylureido-4-p-methoxy-phenoxy-5-nitrophenol moiety (S-4)

To a refluxing solution of 33.7 g (0.2 mol) 2-amino-4-chloro-5-nitrophenol (S-1) and 12.8 g (0.2 mol) potassium hydroxide in 300 ml acetone was added over a 3 hour period 25.3 g (0.2 mol) α-chlorotoluene. After an additional 6 hour reflux, the mixture was concentrated and added to excess cold potassium carbonate solution. The resulting precipitate was washed, dried, and recrystallized from xylene to yield 44.8 g yellow-green solid S-2, m.p. 131°.

A solution of 9.4 g (0.076 mol) p-methoxyphenol and 4.3 g (0.076 mol) potassium hydroxide in 200 ml toluene was refluxed to remove the aqueous azeotrope, then cooled to 40°. Then 40 ml dimethyl sulfoxide and 12 g (0.043 mol) S-2 were added sequentially and the mixture was heated gradually and refluxed 1 hour. The cooled reaction mixture was washed with water and sodium carbonate solution, dried over magnesium sulfate and treated with carbon. The solid obtained by cooling the concentrate and filtering was washed with toluene and hexane, then dried to yield 11.5 g S-3.

This product was converted to S-4 by treatment with equimolar p-cyanophenylisocyanate according to a procedure analogous to that described in Example 1 of U.S. Pat. No. 4,333,999, the disclosure of which is hereby incorporated by reference.

B. Preparation of the Ballast

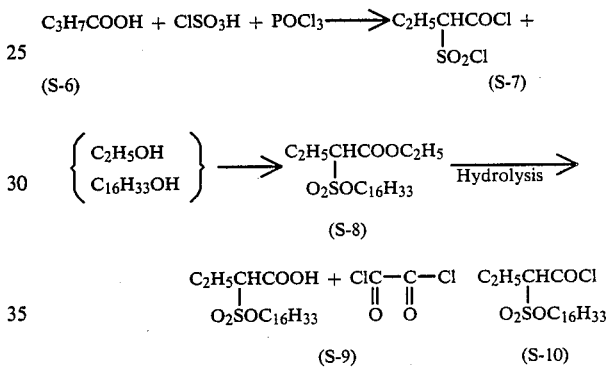

65 ml (1 mole=116 g) of chlorosulfonic acid is added to 183 ml (2 mole=306 g) phosphorous oxychloride with stirring and ice-water cooling. Then 91.7 ml (1 mole=88 g) butyric acid (S-6) is added dropwise over 0.5 hr. while keeping the temperature between 10–15 C.° with continued ice-water cooling. The reaction mixture was allowed to warm to room temperature then slowly heated to reflux. Reflux was continued at about 95° C. for 4 hours during which time the reaction mixture gradually turned black and the reflux temperature increased to 105 C.°. A phosphoric acid by-product precipitated as a gummy solid coating on the sides of the reaction vessel during the course of the reaction. When the reaction mixture had cooled to room temperature, the supernatant black liquid was decanted from the gummy black precipitate and was vacuum distilled. The product (S-7) was recovered at 70–75 C.° under 1.5 mm mercury to yield 125 g of clear colorless liquid. The NMR spectrum was consistent with the expected structure.

To a chilled solution (5 C.°) of 20.5 g (0.10 mol) S-7 in 500 ml anhydrous diethyl ether was added 4.7 g (0.10 mol) ethanol dissolved in 25 ml diethyl ether. The cooling bath was removed and stirring was continued at ambient temperature for 2 hours. Then 36 g (0.15 mol) hexadecyl alcohol was added with stirring until solution was complete. A solution of 25 g (0.25 mol) triethylamine and 15 ml pyridine dissolved in 50 ml diethylether was next added dropwise over a period of 20 minutes as a voluminous white precipitate formed. After 4 hours stirring at ambient temperature, the reaction mixture was washed 3 times with 10% hydrochloric acid. The organic layer was dried and concentrated. Purification by chromotography yielded a clear colorless oil confirmed by a NMR spectrum to be the desired S-8 ester.

4 g (0.10 mol) sodium hydroxide dissolved in 20 ml water was added to a chilled solution (0° C.) of 7 g (0.019 mol) S-8 ester dissolved in a mixture of 60 ml tetrahydrofuran and 40 ml methanol. Stirring was continued at 0° C. for 2 hours. The reaction mixture was then poured into 500 ml of chilled (0° C.) 10% hydrochloric acid and extracted with ethyl acetate. The organic layer was dried and concentrated to a yellow oil which crystallized to yield 6.1 g of product (S-9) as a tan solid.

The S-9 ballast acid was treated with 2.5 g (0.02 mol) oxalyl chloride in 150 ml dichloromethane to yield the ballast acid chloride S-10 as a yellow oil.

C. Coupler formation

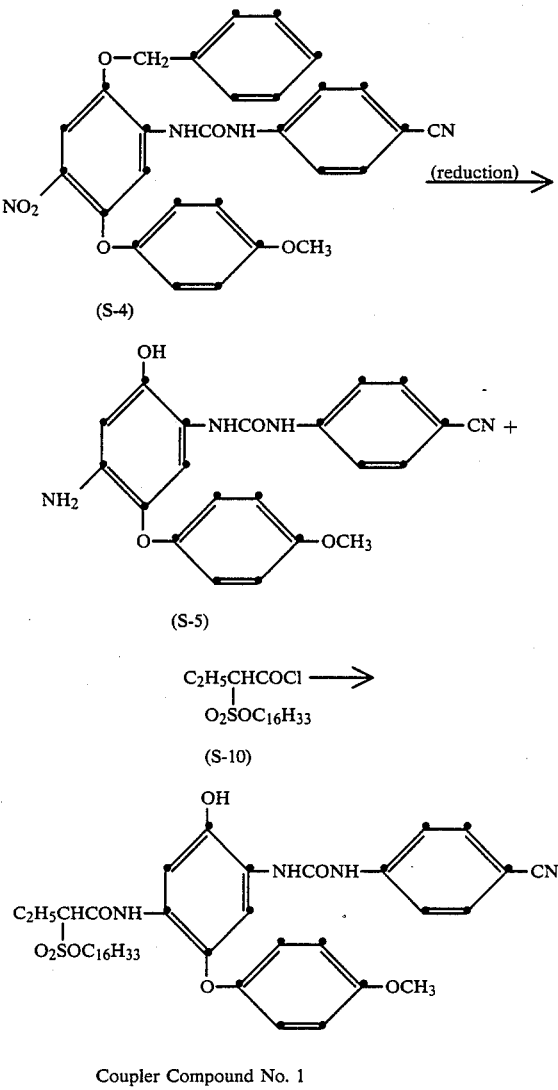

Coupler Compound No. 1

A suspension of 9.4 g (0.0193 mol) nitro compound S-4 (Preparation A above) in ethyl acetate was shaken overnight under 40 psi (276 Pa) hydrogen in the presence of 1.5 g 10% palladium on carbon catalyst and 0.5 ml acetic acid to yield the amino compound S-5. Then 0.0193 mol of ballasted acid chloride S-9 and 7.0 g (0.058 mol) dimethylaniline were added under nitrogen and the mixture was stirred for 15 minutes. After catalyst removal by filtration, the filtrate was washed with dilute hydrochloric acid and concentrated to a solid. Crystallization was effected from acetonitrile to yield 7.1 g of white product as Coupler Compound No. 1 having the correct elemental analysis and mass spectrum.

Preparation of compounds suitable for use in this invention which comprise a sulfamoyl ($-R^4NSO_2-$) group in the ballast moiety can be accomplished by various techniques. For example, intermediate S-7 (as identified above) can be reacted with ethanol and a primary or a secondary amine to obtain the desired intermediate comprising the ethyl ester and a substituted sulfamoyl group. Specifically, the ballast moiety for Compounds 8 and 11 can be obtained by reacting an S-7 intermediate with ethanol and with dodecylamine or with m-nitroaniline where the latter product is reduced to the corresponding amine and derivatized according to procedures well known in the chemical synthesis art.

The cyan dye-forming couplers of this invention can be used in the ways and for the purposes that cyan dye-forming couplers are used in the photographic art. Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent.

As used herein, the term "associated therewith" signifies that the coupler is in the silver halide emulsion layer or in an adjacent location where, during processing, it is capable of reacting with silver halide development products.

The photographic elements can be either single color or multiclor elements. In a multicolor element, the cyan dye-forming coupler of this invention is usually associated with a red-sensitive emulsion, although it could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising of at least one red-sensitive silver halide emulsion layer having associated therewith at least one cyan dye-forming coupler, at least one of the cyan dye-forming couplers being a coupler of this invention, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the elements of this invention, reference will be made to Research Disclosure, December 1978, Item 17643, published by Kenneth Mason Publications, Ltd., The Old Harbourmaster's, 8 North Street, Emsworth, Hampshire P010 7DD, ENGLAND, the disclosures of which are incorporated herein by reference. This publication will be identified hereafter by the term "Research Disclosure."

The silver halide emulsions employed in the elements of this invention can be either negative-working or positive-working. Suitable emulsions and their preparation are described in Research Disclosure Section I and II and the publications cited therein. Tabular photographic silver halide grins are also useful. Such tabular grain silver halide is described in, for example, U.S. Pat. No. 4,434,226 and in *Research Disclosure*, January 1983, Item No. 22534. Suitable vehicles for the emulsion layers and other layers of elements of this invention are described in Research Disclosure Item 17643, Section IX and the publications cited therein.

In addition to the couplers described herein the elements of this invention can include additional couplers as described in Research Disclosure Section VII, paragraphs, D, E, F and G and the publications cited therein. These additional couplers can be incorporated as described in Research Disclosure Section VII, paragraph C and the publications cited therein.

The photographic elements of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methanesulfonamido)ethylaniline sulfate hydrate, 4-amino-3-methyl-N-ethyl-N-$\beta$-hydroxyethylaniline sulfate, 4-amino-3-$\beta$-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

In the following examples, a measure of each coupler's coupling effectiveness is represented by G, the ratio of its photographic dye image gamma (the slope of the sensitometric curve) to that of Control Coupler A, which is normalized to 1.0. Coupler A is identical to Coupler No. 7 of U.S. Pat. No. 4,333,999. Such normalization of the data compensates for coating and processing variations by relating the performance of each test coupler as described herein to that of a control coupler coated and processed at the same time and in the same manner. In these comparisons 2-equivalent couplers were coated at one-half the silver level of 4-equivalent couplers.

Processing and testing procedures were kept constant. Hue measurements on normalized spectral absorption curve included $\lambda$max (the peak absorption wavelength) and HBW (the half bandwidth). The HBW value serves to indicate hue purity. Dye images of narrow HBW and of $\lambda$max$>$675 are least likely to have unwanted absorption tailing into the green region. Particularly useful couplers provided dye images with G$\geq$1.00, $\lambda$max$>$675 nm and HBW$<$140 nm.

The following examples further illustrate this invention.

EXAMPLE 1

Photographic elements were prepared by coating a cellulose acetate film support with a light-sensitive layer comprising a silver bromoiodide emulsion at 0.46 g Ag/m$^2$ (or double their level for Control Coupler A), gelatin at 3.78 g/m$^2$ containing a cyan phenolic coupler identified by number as shown above in Table I. Each coupler was dispersed in one half its weight in di-n-butyl phthalate and coated at $1.62\times10^{-3}$ mols/m$^2$. The photosensitive layer was overcoated with a layer containing gelatin at 1.08 g/m$^2$ and the hardener compound bis-vinylsulfonylmethyl ether at 1.75 weight percent based on total gelatin.

Samples of each element were imagewise exposed through a graduated-density test object and processed at 40° C. employing the following color developing solution, then stopped, bleached with a ferric EDTA (ethylenediaminetetraacetic acid) solution, fixed, and washed to produce stepped cyan dye images.

| | |
|---|---|
| $K_2SO_3$ | 2.0 g |
| $K_2CO_3$ (anhydrous) | 30.0 g |
| KBr | 1.25 g |
| KI | 0.6 mg |
| 4-Amino-3-methyl-N—ethyl N—$\beta$-hydroxyethylaniline sulfate | 3.55 g |
| Water to 1.0 liter | pH 10.0 |

Results are noted below in Table II:

TABLE II

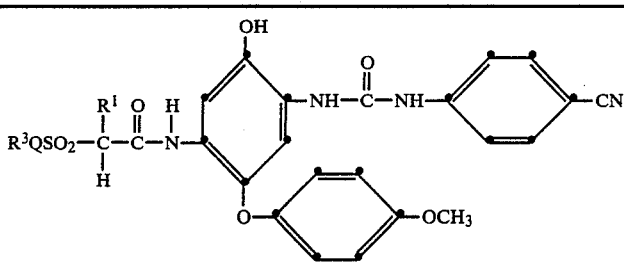

| Coupler Compound No. | $R_1$ | $R_3$ | Q | G | λmax | HBW |
|---|---|---|---|---|---|---|
| Control A | | See Structure | | 1.00 | 695 | 146 |
| 1 | —$C_2H_5$ | —$C_{16}H_{33}$ | —O— | 1.58 | 688 | 138 |
| 8 | —$C_2H_5$ | —$C_{12}H_{25}$ | —NH— | 1.00 | 676 | 130 |
| 11 | —$C_2H_5$ | (phenyl with NHSO$_2$—$C_{16}H_{33}$) | —NH— | 1.54 | 684 | 140 |

*Coupler A:

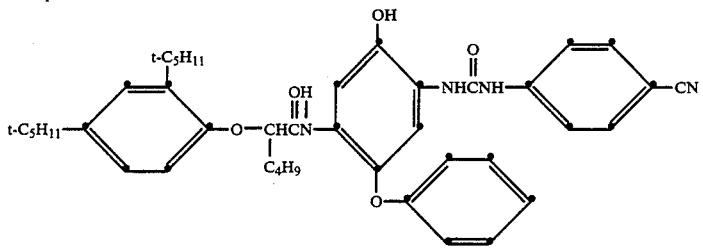

which is Coupler No. 7 in U.S. Pat. No. 4,333,999

From the above results it can be seen that improved hue purity (narrow HBW) is obtained while retaining at least comparable coupling effectiveness values and desired long wavelength (λmax) absorption values in the red region of the visible spectrum.

This invention has been described in detail with particular reference to preferred embodiments thereof, but it will be understood that variations and modifications can be effected within the spirit and scope of the invention.

What is claimed is:

1. A photographic material comprising a support and a photosensitive silver halide emulsion which has associated therewith a cyan dye-forming coupler compound having the structural formula:

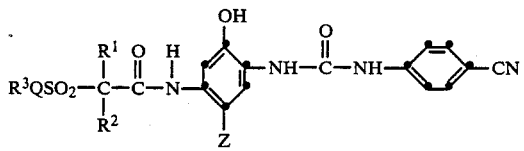

wherein:

Q is —O— or —$NR^4$—;

$R^1$ is an unsubstituted or substituted, straight or branched chain alkyl group having from 1 to about 20 carbon atoms, an unsubstituted or substituted cycloalkyl group having from 3 to about 8 carbon atoms in the ring, an alkylcarbonyl or an alkoxycarbonyl group having from 1 to about 20 carbon atoms in the alkyl or the alkoxy moiety;

$R^2$ is as defined for $R^1$ or is hydrogen;

$R^3$ is an unsubstituted or a substituted alkyl group having from 1 to about 24 carbon atoms, an unsubstituted or a substituted cycloalkyl group having from 3 to about 8 carbon atoms in the ring, an unsubstituted or a substituted aryl group having from 6 to about 24 carbon atoms, or an unsubstituted or a substituted heterocyclic group having from 3 to about 8 atoms in the heterocyclic ring, wherein the hetero ring atoms can be nitrogen, oxygen, or sulfur;

with the proviso that when $R^3$ is a primary alkyl group $R^1$ must contain at least 2 carbon atoms;

$R^4$ is hydrogen; an unsubstituted or a substituted alkyl group having from 1 to about 24 carbon atoms, an unsubstituted or a substituted cycloalkyl group having from 3 to about 8 carbon atoms in the ring, or an unsubstituted or a substituted aryl group having from 6 to about 24 carbon atoms; and Z is hydrogen or a coupling off group.

2. The photographic material of claim 1 wherein Q is —$NR^4$—.

3. The photographic material of claim 2 wherein $R^4$ is hydrogen.

4. The photographic material of claim 1 wherein Q is —O—.

5. The photographic material of claim 1 wherein $R^1$ is alkyl of from 1 to about 20 carbon atoms and $R^2$ is alkyl of from 1 to about 4 carbon atoms.

6. The photographic material of claim 1 wherein $R^1$ is alkyl of from 1 to about 14 carbon atoms and $R^2$ is hydrogen.

7. The photographic material of claim 1 wherein at least one of $R^1$ and $R^2$ is substituted with hydroxy, a halogen atom or an alkoxy group having from 1 to about 8 carbon atoms.

8. The photographic element of claim 1 wherein Z is hydrogen or

where $R^5$ is an alkyl or an alkoxy group having from 1 to about 10 carbon atoms.

9. The photographic material of claim 1 wherein the cyan dye-forming coupler compound has the structural formula:

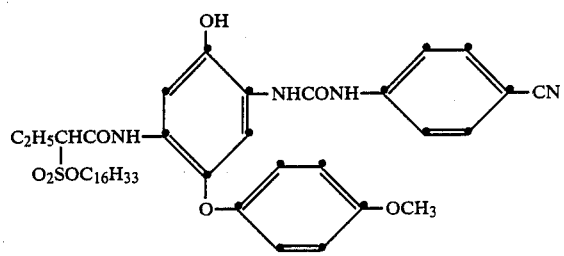

10. The photographic material of claim 1 wherein the cyan dye-forming coupler compound has the structural formula:

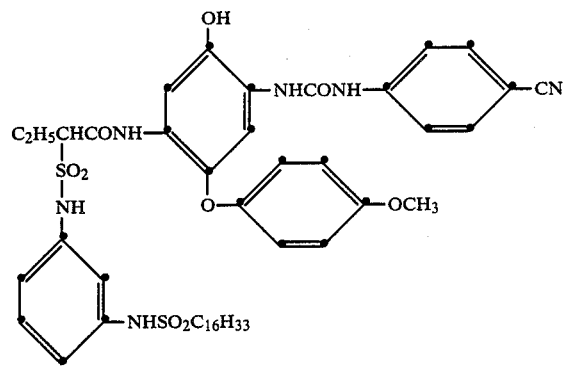

11. The photographic material of claim 1 wherein the cyan dye-forming coupler compound has the structural formula:

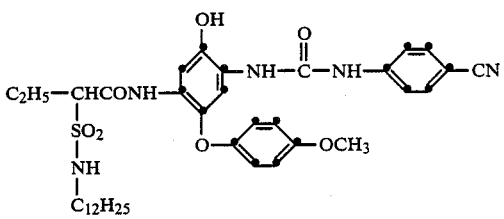

* * * * *